United States Patent [19]

Davidson

[11] 4,379,506
[45] Apr. 12, 1983

[54] CATHETER ASSEMBLY

[76] Inventor: Alan C. Davidson, 15 Edgehill Dr., Woodbridge, Conn. 06525

[21] Appl. No.: 250,239

[22] Filed: Apr. 2, 1981

[51] Int. Cl.³ .................... B65D 27/36; B65D 85/08
[52] U.S. Cl. .................................. 206/364; 206/438
[58] Field of Search .............. 206/364, 363, 438, 440; 15/227

[56] References Cited

U.S. PATENT DOCUMENTS

| 2,856,932 | 10/1958 | Griffitts | 128/294 |
|---|---|---|---|
| 3,062,371 | 11/1962 | Patience | 206/440 |
| 3,638,789 | 2/1972 | Tuszewski | 206/438 |
| 3,683,928 | 8/1972 | Kuntz | 128/349 |
| 3,898,993 | 8/1975 | Taniguchi | 128/349 |
| 3,926,309 | 12/1975 | Center | 206/364 |
| 3,930,580 | 1/1976 | Bazell et al. | |
| 3,934,721 | 1/1976 | Juster et al. | 206/364 |
| 4,116,338 | 9/1978 | Weichselbaum | 206/363 |
| 4,140,127 | 2/1979 | Cianci et al. | 128/349 |

OTHER PUBLICATIONS

Article–"Clean, Intermittent Self-Catheterization in the Treatment of Urinary Tract Disease", The Journal of Urology, vol. 107, Mar. 1972.
Article–"Experience With Non-Sterile Intermittent Self-Catheterization", The Journal of Urology, vol. 115, Feb. 1976.

Primary Examiner—William T. Dixson, Jr.
Attorney, Agent, or Firm—St. Onge, Steward, Johnston & Reens

[57] ABSTRACT

A catheter assembly is described in which a catheter within a package can be extracted and utilized in a sterile manner which is particularly useful for a self-catheterization procedure. As described with reference to one embodiment, the catheter assembly is formed with a bottom layer and a top layer between which the catheter is located in a sterile manner. The top layer is provided with a backing so as to form a pocket in which one can place a hand and grip the catheter through the top layer. Sterile packets of lubricating jelly and antiseptic wipe may be placed here. The bottom and top layers are joined along a tear zone so that the layers can be separated from each other while gripping the catheter through the top layer and pulling the bottom layer away so that upon separation, one holds the catheter in a sterile manner. In one form, the bottom layer is in the form of a bag to which one end of the catheter is connected so that the urine may drain into it.

10 Claims, 11 Drawing Figures

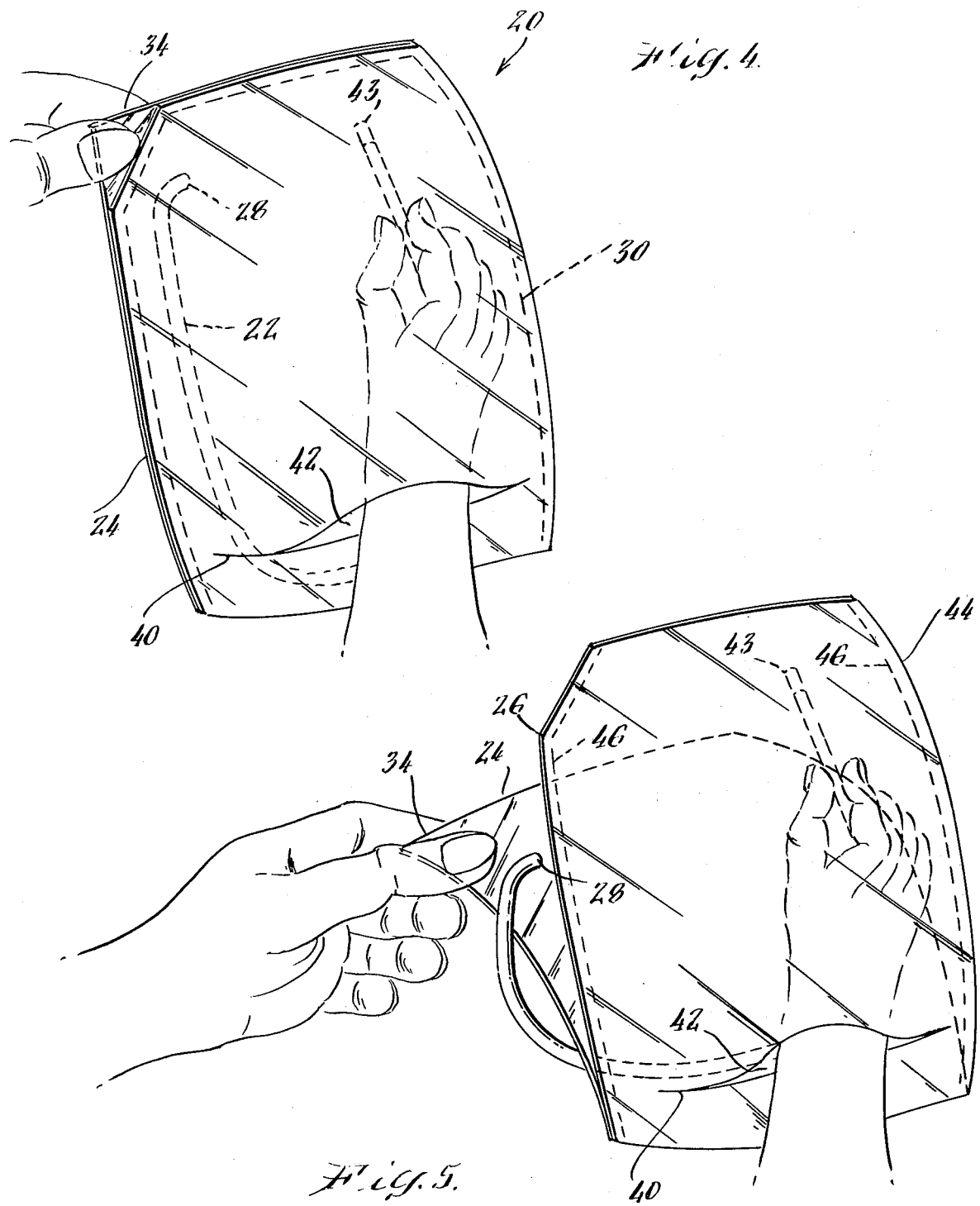

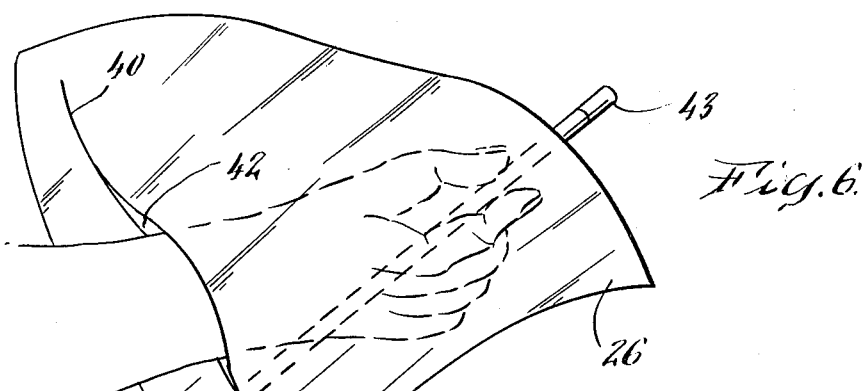
Fig. 6.
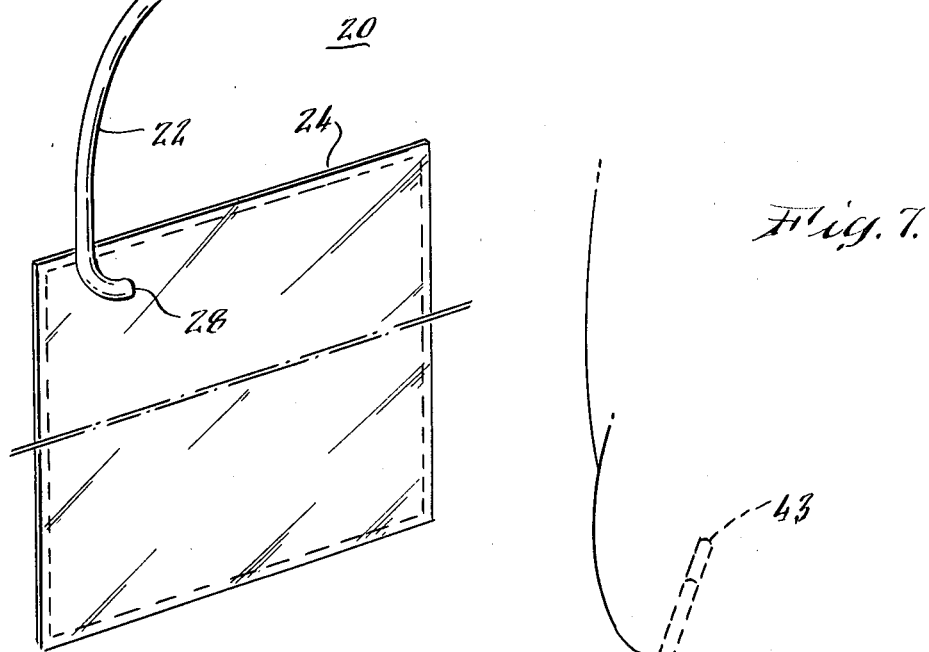
Fig. 7.
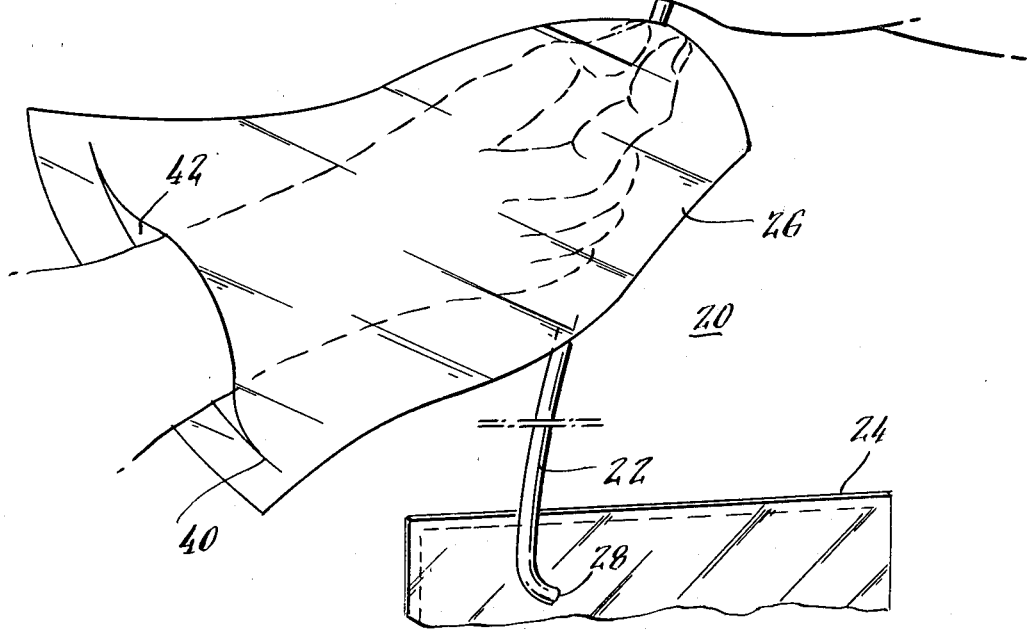

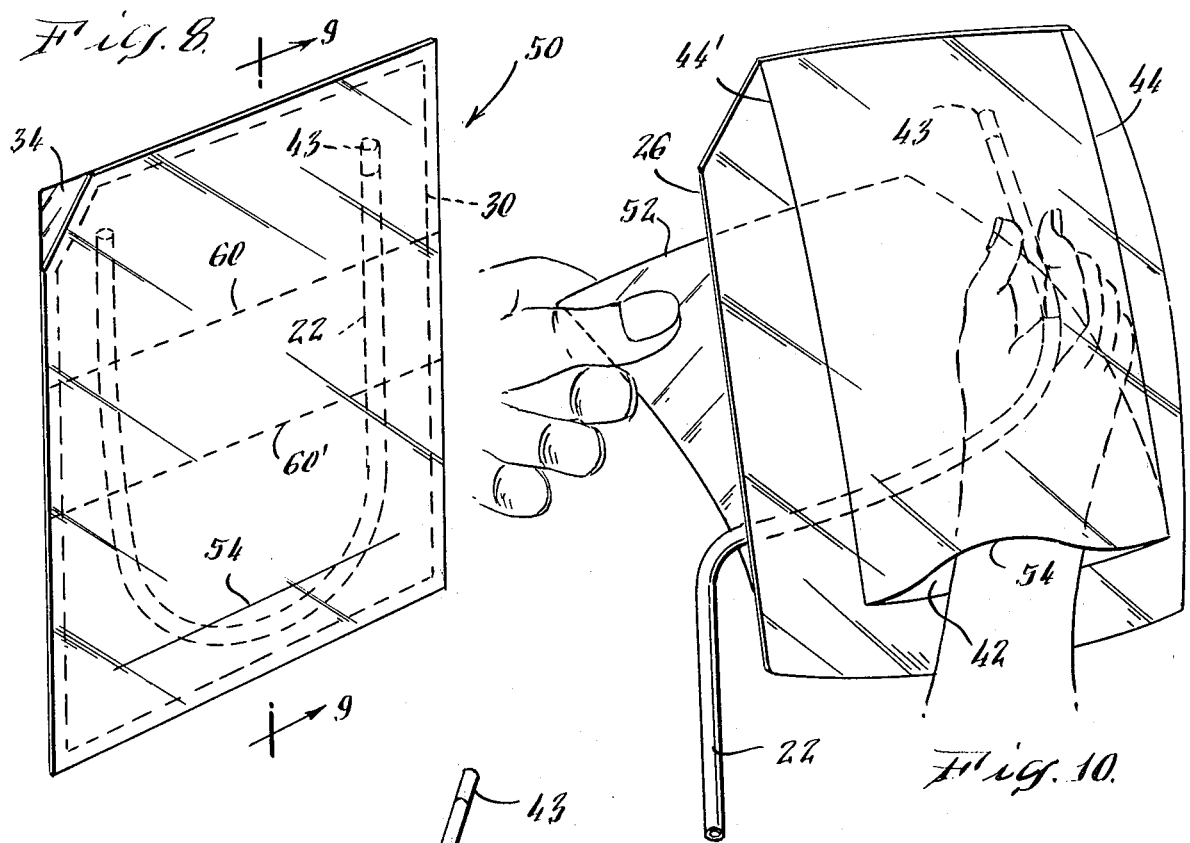

CATHETER ASSEMBLY

FIELD OF THE INVENTION

This invention relates to a package assembly for devices such as medical catheters and the like. More specifically, this invention relates to a catheter assembly for use in the self catheterization of the urinary tract.

BACKGROUND OF THE INVENTION

Sterile packaging of medical devices has been extensively developed. These devices may encompass a broad range of products, such as syringes, needles, bandages, catheters and many others. Particular sterile care must be undertaken with regard to the use of catheters intended to be inserted through body openings. When a catheter is employed to aid in urethral catherization, precautions need to be taken to avoid introduction of infection carrying bacteria. Since such catherization is for some people the only available technique to void their urine, self-catheterization devices and techniques would be particularly useful for active persons as compared to otherwise in-dwelling type catheter devices. See, for example, an article entitled "Experience With Non-Sterile, Intermittent Self-Catheterization" by Orikasa et al, published at page 141 in Volume 115 of the February 1976 issue of The Journal of Urology by the Williams & Wilkins Co. Another article related to self-catheterization was published in The Journal of Urology, Vol. 107, March 1972, page 458, by Lapides et al, under the title "Clean Intermittent Self-Catheterization In The Treatment Of Urinary Tract Disease".

As described in the first article, a patient carries a catheter which, before use, is washed and occasionally sterilized by boiling. The patient employs the catheter a number of times on a daily basis, thereby improving comfort and correcting physiological conditions. However, sterility is not always maintained. In order to take advantage of the intermittent self-catheterization procedure, the use of disposable sterile catheters in a sterile manner would enhance the benefit of such self-catheterization procedure.

Sterile packages of catheters for use in their subsequent sterile handling are well known in the art. For example, in the U.S. Pat. No. 4,140,127 to Cianci et al, a package encloses a sterile catheter assembly formed of an elongated flexible sleeve having a folded back cuff which surrounds the distal tip of a urethral catheter. Upon opening of the package to break the sterile barrier, one can grip the catheter at its distal end through the sleeve and under the cuff for sterile handling. A disadvantage of the Cianci et al package is that the catheter is not continuously gripped from the time that the sterile barrier is broken so that inadvertent contamination of the catheter distal tip may occur.

In U.S. Pat. No. 3,930,580 to Bazell et al, a sterile catheter package is taught wherein a catheter is placed in a pouch formed between two sheets which are joined at separable edges. The catheter is removable by separating one sheet from another along tear zones located at opposite edges of the sheets. A tab is connected to one sheet so that one may, by holding the tab in one hand, on one side of a score line while holding the package on the other side of the score line with the other hand, pull the sheets apart.

In the U.S. Pat. No. 3,934,721 to Juster et al, a sterile catheter package is shown wherein a catheter package is located within an overpackage. U.S. Pat. No. 3,926,309 to Center shows a multicompartmented sterile catheter package and U.S. Pat. Nos. 3,683,928 to Kuntz and 3,898,993 to Taniguchi show sterile catheter packages with catheter lubricants. U.S. Pat. No. 2,856,932 to Griffits teaches the attachment of a sterile packaged urethral catheter attached to a bag in which urine may be collected.

While these sterile catheter packages may be useful for the removal and use of the catheters, they may be cumbersome to use and particularly difficult to keep a catheter uncontaminated for a self-catheterization procedure.

SUMMARY OF THE INVENTION

In a catheter assembly in accordance with the invention, a catheter is placed between top and bottom layers which are releasably attached to each other along a tear line. The top layer is sufficiently strong and flexible to enable one to manually and firmly grip the catheter at its distal end through the layer with one hand, while tearing away the bottom layer with the other hand, so that upon separation of the layers, the catheter is retained in a sterile manner by the one hand through the top layer whereby sterile handling of the catheter is assured and, in particular, a self-catheterization procedure is less likely to contaminate the catheter.

As described herein for one form of a catheter assembly in accordance with the invention, a catheter is placed between top and bottom layers which are joined to one another along a tear line to enclose the catheter in a sterile protective manner. The top layer is provided with a backing on an externally exposed side. The backing is so placed to overly this layer that a hand can be placed between the backing and the top layer so as to grip the catheter through this layer while enabling the back of the hand to serve as a restraint on the top layer as the bottom layer is torn away by the other hand. The backing may be a band or a sheet which forms a pocket sized to receive a hand for gripping of the catheter to aid in the separation of the catheter enclosing layers.

With a catheter assembly in accordance with the invention, sterile catheter handling is facilitated with a disposable assembly thus lessening the chances for contamination and resulting infection, particularly in self-catheterization procedures. A packaging assembly in accordance with the invention may be used with other medical devices which require sterile handling.

It is, therefore, an object of the invention to provide a medical device assembly which allows easy removal from a sterile package and subsequent manipulation of the device while preserving its sterility. It is a further object of the invention to provide a catheter assembly with which a self-catheterization procedure can be obtained with less chance for an infection.

These and other advantages and objects of the invention can be understood from the following detailed description of embodiments described in conjunction with the drawings.

BRIEF DESCRIPTION OF DRAWINGS

FIGS. 4, 5, 6 and 7 are perspective views of sequential steps in the use of the catheter assembly as shown in FIG. 1;

FIG. 8 is a perspective view of a modified form for a catheter assembly in accordance with the invention;

FIG. 9 is a vertical sectional view of the catheter assembly in FIG. 8 and is taken along the lines 9—9 therein; and FIGS. 10 and 11 are perspective views of the sequential steps in the use of the catheter assembly as shown in FIG. 8.

DETAILED DESCRIPTION OF EMBODIMENTS

Figure 1:
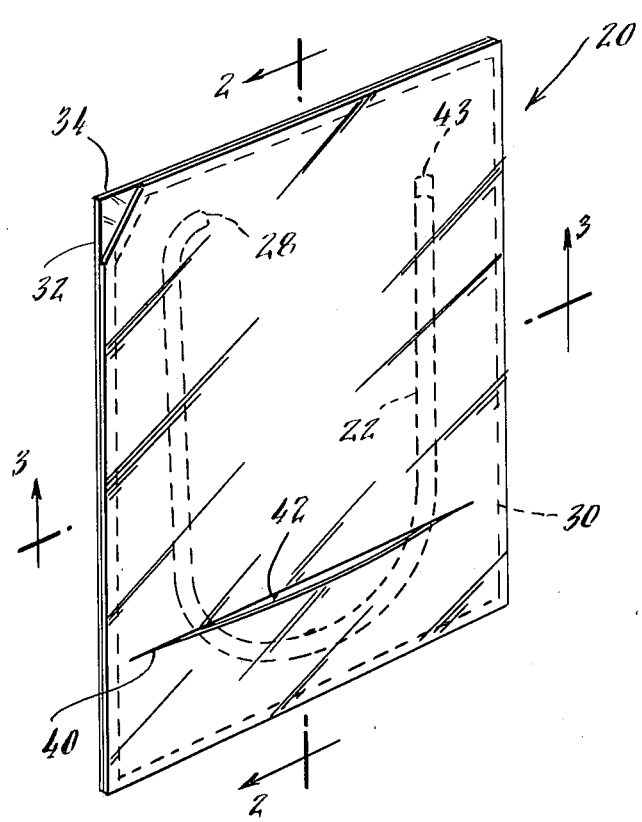
FIG. 1 is a perspective view of a catheter assembly in accordance with the invention.
Figure 2:
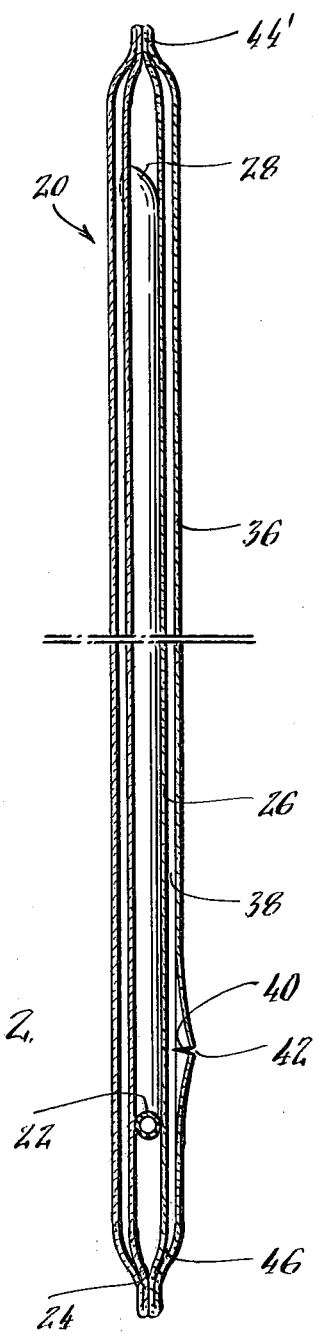
FIG. 2 is a vertical section view of the catheter assembly of FIG. 1 taken along the lines 2—2 therein.
Figure 3:
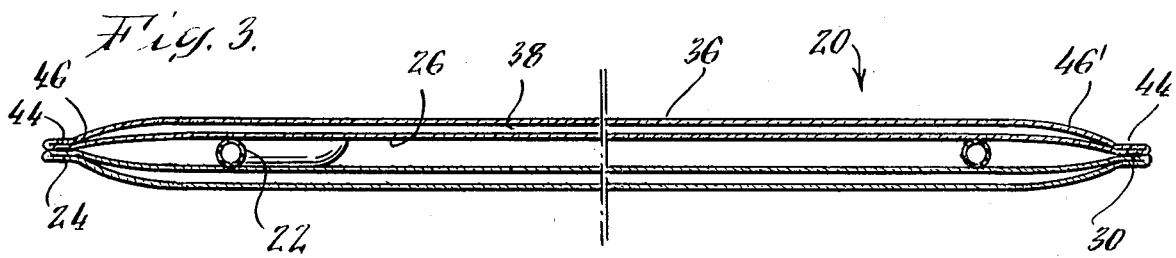
FIG. 3 is a horizontal sectional view of the catheter assembly of FIG. 1 taken along the lines 3—3 therein.

With reference to FIGS. 1-3, a catheter assembly 20 is shown wherein a urethral catheter 22 is enclosed by a bottom layer 24 and top layer 26. The bottom layer 24 is in the form of a bag to which a proximal end 28 of the catheter 22 is attached to pass the urine into when the catheter is employed. The top layer 26 is releasably attached to bottom layer 24 along a tear line 30 so that the layers 24, 26 can be separated from each other. The top layer 26 is cut away at 32 to expose a corner tab 34 of the bottom layer 24 for use in its separation from the top layer 26.

A backing 36 is affixed to top layer 26 to form a pocket 38 between top layer 26 and backing 36. The backing either is slit at 40 or terminates along the line formed by slit 40 so that an opening 42 is made into pocket 38 with sufficient size to receive a hand.

The catheter assembly 20 may be formed so as to provide a selfcontained sterile package or fit again into such other package (not shown) as may appear desirable. If desired, a sterile package of lubricating jelly and antiseptic wipe may be placed inside the sterile package. In either case the catheter 22 is located between top and bottom layers 24, 26 which provide protection against bacterial contamination so that the sterility of the catheter is preserved. For example, the bottom layer 24 may be formed of a gas permeable, though bacteria impermeable, material for gas sterilization of the assembly 20.

The top layer 26 is formed of a material which preserves the sterility of the catheter 22 and is further made sufficiently flexible to enable one to grip the catheter 22 through the top layer 26. The flexibility of top layer 26 may be achieved by making it of a thin sheet material through which one can firmly grasp the catheter, for example near its distal end 43. Yet the material should be of sufficient strength so that despite the formation of wrinkles and sharp folds when grasping catheter 22, the integrity of the top layer 26 is maintained and thus the catheter 22 remains uncontaminated. Materials suitable for the formation of top layer 26 are well known and reference can be had to the aforementioned patents for further details.

The backing 36 is formed of a sheet material which is firmly bonded at its peripheral edge 44 to top layer 26. Backing 36 may be part of the same sheet which forms top layer 26 in which case backing 36 may be folded over at edge 44' and fusion bonded to top layer 26 along a zone 46. The bonded zone 46 is preferably close to tear line 30 so that a hand in pocket 38 can, while grasping catheter 22, restrain top layer 26 while the bottom layer 24 is being pulled away. The backing sheet 36 is preferably so sized that the pocket 38 formed with top layer 26 enables one to grip the catheter 22 while providing sufficient restraint on the edges of the top layer 26 through contact of the back of the hand with the backing 36 that separation of layers 24, 26 along tear line 30 is facilitated.

In the use of a catheter assembly in accordance with the invention and particularly when employed for a self-catheterization procedure, one hand is inserted through opening 40 into the pocket 38 and the catheter 22 firmly grasped as illustrated in FIG. 4. The other hand engages tab 34 of bottom layer 24.

The bottom layer 24 is then pulled away from top layer 26 along the tear line 30 as shown in FIG. 5 until the layers are entirely separated from each other as illustrated in FIG. 6. At that time the catheter 22 is firmly held in a sterile manner through the top layer 26 while the liquid collection bag formed by the bottom layer 24 is suspended from end 28 of catheter 22.

One may then manipulate catheter 22 for a self-catheterization, for example, as shown in FIG. 7 without physical contaminating contact with the catheter 22. Note that the opening 42 and the distal end 43 of catheter 22 are so located and spaced from each other that when the hand is inserted into opening 42, the catheter can be initially grasped at the desired location for manipulation and final use as may appear necessary. In the embodiments shown, the catheter 22 lies in a U-shaped bend with the distal end portion of the catheter 22 facing away from the opening 42 or in a direction in which one approaches the catheter 22 for grasping.

With reference to FIGS. 8-11 a catheter assembly 50 in accordance with the invention is shown wherein bottom layer 24 is formed of a sheet 52 which, with top layer 26, encloses catheter 22. The latter is not connected to a bag but lies loosely between the sheet 52 and top layer 26. A backing 54 is provided which is a fold-over portion of the top layer sheet 26. The backing edges 44-44' are bonded to top layer 26 to form a pocket 38 for insertion of a band as shown.

The backing 54 is of reduced width to form a sufficiently small pocket 38 to facilitate separation of layers 52, 26 while still being sufficiently large to enable grasping of catheter 22 near its distal end.

The backing could be formed of a single sheet band or multiple number of such bands as suggested with dotted lines 60-60'.

Having thus explained several embodiments for a catheter assembly in accordance with the invention, its advantages can be understood. Variations from the description can be made without departing from the scope of the invention as set forth in the following claims.

What is claimed is:

1. A package assembly for storing a device such as catheters and the like in a sterile manner while enabling manual removal of the device without breaking its sterility, comprising:

a bottom layer underlying the device;
a top layer overlying the device and the bottom layer and being releasably attached to the top layer to retain the device between the layers, said bottom and top layers being formed of a material enabling the protection of the device against contamination, said top layer further being sufficiently flexible while attached to the bottom layer to enable one to manually grip the device through said top layer while attached to the bottom layer, said top layer being separable from said bottom layer while gripping the device with one hand through the top layer and tearing away the bottom layer from the top layer with the other hand;

said top layer being provided with a backing located on a side opposite to the bottom layer, said backing being attached to said top layer at spaced locations selected to enable said one hand to fit between the backing and the top layer to permit the back of said hand to restrain said top layer as the bottom layer is torn away in a direction away from said hand, whereby upon said layer separation said device is exposed for use while being held in a sterile manner by said one hand through the separated top layer.

2. The package assembly as claimed in claim 1 wherein said device is so oriented with respect to said backing that said hand may approach to grip said device along a direction desired for manipulation of the device through said top layer while maintaining said device uncontaminated.

3. The package assembly as claimed in claim 1 or 2 wherein said backing is sized to form an externally accessible pocket sized to receive said one hand while enabling gripping of the device through the top layer.

4. The package assembly as claimed in claim 1 or 2 wherein the backing is in the form of a band which is attached at its ends to the top layer.

5. The package assembly as claimed in claim 1 wherein said backing is attached to the top layer to form an externally accessible pocket therewith sized to receive said one hand.

6. A catheter assembly comprising:
 a bottom layer underlying the catheter;
 a top layer of thin flexible material overlying the catheter and the bottom layer and being releasably attached along a tear line to the bottom layer to retain the catheter between the layers, said top and bottom layers being formed of a material selected to protect the catheter against contamination, said top layer further being sufficiently flexible and moveable while attached to the bottom layer to enable one to manually grip the catheter through said top layer while it is attached to the bottom layer, said top layer further being separable from the bottom layer while gripping the catheter with one hand through the top layer and tearing away the bottom layer from the top layer with the other hand,
 said top layer being provided with a backing located on a side opposite to the bottom layer, said backing being attached to said top layer at spaced locations selected to enable said one hand to fit between the backing and the top layer and enable the back of said one hand to restrain the top layer at said tear line as the bottom layer is torn away in a direction away from said top layer, whereby upon said separation the catheter is exposed for use while being held in a sterile manner by said one hand through the top layer.

7. The catheter assembly as claimed in claim 6 wherein said catheter is so oriented with respect to said backing so as to enable said one hand to approach the catheter along a direction desired to be able to grip the catheter for sterile manipulation through said top layer.

8. The catheter assembly as claimed in claims 6 or 7 wherein said bottom layer is a bag, with one end of said catheter being attached to the bag to enable the flow of liquid into said bag through the catheter.

9. The catheter assembly as claimed in claim 6 wherein said backing is sized to form an externally accessible pocket sized to receive said one hand while enabling gripping of the catheter through the top layer.

10. A catheter assembly comprising:
 a bottom layer underlying a catheter in the form of a liquid retaining bag affixed to one end of said catheter to enable the flow of liquid into said bag through the catheter;
 a top layer of thin flexible material overlying the catheter and the bottom layer and being releasably attached along a tear line to the bottom layer to retain the catheter between the layers, said top and bottom layers being formed with a material selected to protect the catheter against contamination, said top layer further being sufficiently flexible and moveable while attached to the bottom layer to enable one to manually grip the catheter through said top layer while it is attached to the bottom layer, said top layer further being separable from the bottom layer while gripping the catheter with one hand through the top layer and tearing away the bottom layer from the top layer with the other hand, whereby upon said separation the catheter is exposed for use while being held in a sterile manner by said one hand through the top layer.

* * * * *